United States Patent [19]

Butman et al.

[11] Patent Number: 5,514,541

[45] Date of Patent: May 7, 1996

[54] T-LYMPHOTROPIC RETROVIRUS MONOCLONAL ANTIBODIES

[75] Inventors: Bryan T. Butman, Walkersville; Thomas M. Venetta, Derwood, both of Md.

[73] Assignee: Akzo Nobel N.V., Arnhem, Netherlands

[21] Appl. No.: 304,977

[22] Filed: Sep. 13, 1994

Related U.S. Application Data

[60] Continuation of Ser. No. 44,340, Apr. 7, 1993, abandoned, which is a division of Ser. No. 825,447, Jan. 23, 1992, Pat. No. 5,210,181, which is a continuation of Ser. No. 351,882, May 15, 1989, abandoned.

[51] Int. Cl.$^6$ .................................................. G01N 33/53
[52] U.S. Cl. ........................ 435/5; 435/7.1; 435/7.92; 435/7.93; 435/7.94; 435/7.95; 435/974; 530/326; 530/388.3; 530/388.35; 530/806
[58] Field of Search .................... 435/5, 7.1, 7.9–7.95, 435/974; 530/326–328, 300, 806, 388.3, 388.35

[56] References Cited

U.S. PATENT DOCUMENTS

| | | |
|---|---|---|
| 4,775,457 | 7/1988 | Robert-Guroff et al. |
| 4,843,011 | 6/1989 | Sarngadharan et al. |
| 4,886,742 | 12/1989 | Kortright et al. |
| 4,888,290 | 12/1989 | Kortright et al. |
| 5,081,226 | 1/1992 | Berzofsky et al. |

OTHER PUBLICATIONS

Niedrig et al. "Monoclonal Antibodies . . . Virus" J. Gen. Virol. 69:2109–2114 (Aug. 1988).
Minassian et al. "Monoclonal Antibodies . . . Simion Immunodiciancy Virus" PNAS 85:6939–6943 (Sep. 1988).
Di Marzo Veronese et al., Biol. Abstr., 80(10):AB587, #87756, Nov. 15, 1985.
T. Hattori et al., Biol. Abstr., 84(1):AB499, #4459, Jul. 1, 1987.
P. Kusk et al., Biol. Abstr., 87(10):AB1146, #110752, May 15, 1989.
F. Chavel et al., Science, 233:342–346, Jul., 1986.
A. Coates et al., Nature, 326:549–550, Apr., 1987.
M. Guyader et al., Nature, 326:662–669, Apr., 1987.
H. A. Kessler et al., JAMA, 258:9:1196–1199, Sep., 1987.
G. Kohler et al., Nature, 256:495–497, 1987.
H. Kühnel et al., Proc. Natl. Acad Sci, USA, 86:2383–2387, Apr., 1989.
R. G. Marlink et al., Aids Research and Human Retroviruses, 4:2:137–148, 1988.
A. A. Minassian et al., Proc. Natl. Acad. Sci. USA, 85:6939–6943, Sep., 1988.
P. S. Meissner et al., Proc. Natl. Acad. Sci. USA, 84:4161–4175, Jun. 1987.
M. Robert-Guroff et al., Science, 215:975–978, Feb., 1982.
M. G. Sarngadharan et al., Science, 224:506–509, May, 1984.
B. R. Starcich et al., Cell, 45:637–648, Jun. 1986.
H. Towbin et al., Proc. Natl. Acad. Sci. USA, 76:9:4350–4354, Sep., 1979.
R. A. Wall et al., The Lancet, p. 566, Mar. 7, 1987.
R. A. Weiss et al., AIDS, 2:2:95–99, 1988.
C. J. Marcus-Sekura et al., Biochemics et Biophysica Acta, 949:213–223, 1988.
D. J. Dowbenko et al., Proc. Natl. Acad. Sci. USA, 82:7748–7752, Nov., 1985.
M. Alizon et al., Cell, 46:63–74, Jul., 1986.
L. Chakrabarti et al., Nature, 328:543–547, Aug., 1987.
E. H. Beachey et al., The Journal of Immunology, 136:6:2287–2292, Mar., 1986.
A. Meyerhans et al., Cell, 58:901–910, Sep., 1989.

Primary Examiner—Christine M. Nucker
Assistant Examiner—Jeffrey Stucker
Attorney, Agent, or Firm—Mary E. Gormley

[57] ABSTRACT

The present invention relates to monoclonal antibodies, cell lines producing the monoclonal antibodies, assays using the antibodies for the detection of HIV-1 and HIV-2 gene products, and diagnostic kits. More particularly, the monoclonal antibodies react with the p24/p26 capsid protein. Assays using monoclonal antibodies that can simultaneously detect HIV-1 and HIV-2 are disclosed.

12 Claims, 12 Drawing Sheets

```
                    142                                                                              158
HIV-1_RF:      -Gln-Met-Val-His-Gln-Ala-Ile-Ser-Pro-Arg-Thr-Leu-Asn-Ala-Trp-Val-Lys-Val-Val-    +

HIV-2_NIH-Z:   -Asn-Tyr-Thr-His-Ile-Pro-Leu-Ser-Pro-Arg-Thr-Leu-Asn-Ala-Trp-Val-Lys-Leu-Val-    +

SIV_MAC:       -Asn-Tyr-Thr-His-Leu-Pro-Leu-Ser-Pro-Arg-Thr-Leu-Asn-Ala-Trp-Val-Lys-Leu-Val-    +
```

1 2 3 4 5   6 7 8 9 10   11 12 13 14

15 16 17 18   19 20 21 22 23   24 25 26

CROSS-REACTIVITY OF ANTI-p24 Mabs WITH p26 OF HIV-2

| STRIP | MAB |
|---|---|
| 1 | Hu-anti-HIV-1 IgG |
| 2 | OSS 39-B-3 |
| 3 | MOPC 21 (IgG1) |
| 4 | F86/ 5-B4 |
| 5 | 5-D9 |
| 6 | 6-C10 |
| 7 | 7-E10 |
| 8 | 5-E2 |
| 9 | 9-B7 |
| 10 | 7-F3 |
| 11 | 6-F6 |
| 12 | 9-D5 |
| 13 | 7-D4 |
| 14 | 6-E11 |
| 15 | 7-E1 | rp24 PEPTIDE gag 24.5
| 133                    363 | gag 8
| 209         363 | gag 126
| 142            344 | gag 141
| 209 263 | gag 107
| 209 242 |

FIG. 4 gag OPEN READING FRAME, AMINO ACID
RESIDUES 133-363

| 133 | 142 | 209 | 263 | 344 | 363 |
| A | B | | | C | D | p24

FIG. 5

WESTERN BLOT ANALYSIS OF ANTI-p24 MAb

WESTERN BLOT ANALYSIS OF ANTI-p24 MAb

| NONAPEPTIDE FRACTION | AMINO ACID SEQUENCE | ELISA |
|---|---|---|
| 61 | Gln-Met-Val-His-Gln-Ala-Ile-Ser-Pro | − |
| 62 | Met-Val-His-Gln-Ala-Ile-Ser-Pro-Arg | + |
| 63 | Val-His-Gln-Ala-Ile-Ser-Pro-Arg-Thr | + |
| 64 | His-Gln-Ala-Ile-Ser-Pro-Arg-Thr-Leu | + |
| 65 | Gln-Ala-Ile-Ser-Pro-Arg-Thr-Leu-Asn | + |
| 66 | Ala-Ile-Ser-Pro-Arg-Thr-Leu-Asn-Ala | + |
| 67 | Ile-Ser-Pro-Arg-Thr-Leu-Asn-Ala-Trp | + |
| 68 | Ser-Pro-Arg-Thr-Leu-Asn-Ala-Trp-Val | − |
| 69 | Pro-Arg-Thr-Leu-Asn-Ala-Trp-Val-Lys | + |
| 70 | Arg-Thr-Leu-Asn-Ala-Trp-Val-Lys-Val | + |
| 71 | Thr-Leu-Asn-Ala-Trp-Val-Lys-Val-Val | − |

COMPOSITE (amino acid residues 142-158):

V-1RF:-Gln-Met-Val|His|Gln-Ala-Ile|Ser-Pro-Arg-Thr-Leu=Asn-Ala-Trp-Val-Lys|Val|Val| +

```
                            142                                                    158
HIV-1_RF:     -Gln-Met-Val-His-Gln-Ala-Ile-Ser-Pro-Arg-Thr-Leu-Asn-Ala-Trp-Val-Lys-Val-Val-  +

HIV-2_NIH-Z:  -Asn-Tyr-Thr-His-Ile-Pro-Leu-Ser-Pro-Arg-Thr-Leu-Asn-Ala-Trp-Val-Lys-Leu-Val-  +

SIV_MAC:      -Asn-Tyr-Thr-His-Leu-Pro-Leu-Ser-Pro-Arg-Thr-Leu-Asn-Ala-Trp-Val-Lys-Leu-Val-  +
```

FIG. 9

```
                          142                                                              158
HIV-1_RF:     -Gln-Met-Val-His-Gln-Ala-Ile-Ser-Pro-Arg-Thr-Leu-Asn-Ala-Trp-Val-Lys-Val-Val-
                                                                                          +
HIV-2_NIH-Z:  -Asn-Tyr-Thr-His-Ile-Pro-Leu-Ser-Pro-Arg-Thr-Leu-Asn-Ala-Trp-Val-Lys-Leu-Val-
                                                                                          +
SIV_MAC:      -Asn-Tyr-Thr-His-Leu-Pro-Leu-Ser-Pro-Arg-Thr-Leu-Asn-Ala-Trp-Val-Lys-Leu-Val-
                                                                                          +
```

FIG. 9

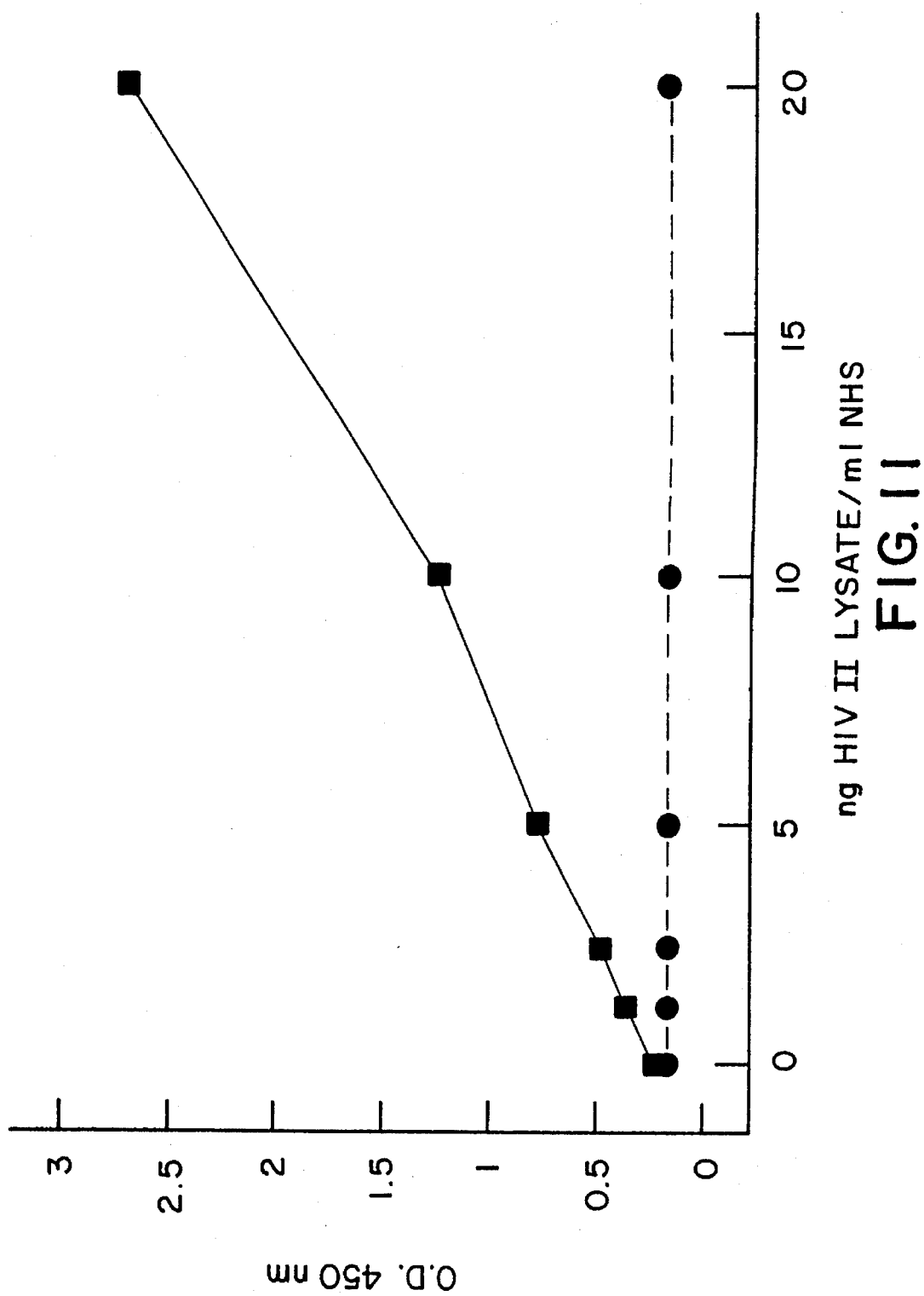

T-LYMPHOTROPIC RETROVIRUS MONOCLONAL ANTIBODIES

This is a continuation of U.S. Ser. No. 08/044,340 filed Apr. 7, 1993, now abandoned, which is a divisional of U.S. Ser. No. 07/825,447, filed Jan. 23, 1992, now U.S. Pat. No. 5,210,181, which is a file wrapper continuation of U.S. Ser. No. 07/351,882 filed May 15, 1989, now abandoned.

FIELD OF THE INVENTION

The invention relates to monoclonal antibodies, peptides that comprise the epitopes of said monoclonal antibodies and assays utilizing said monoclonal antibodies and said peptides for the detection of T-lymphotropic retroviruses, particularly HIV-1, HIV-2 and SIV.

BACKGROUND OF THE INVENTION

The T-lymphotropic retrovirus family includes among other lentiviruses the simian retrovirus SIV and the human retroviruses HIV-1 (the likely etiologic agent of AIDS) and HIV-2. Although HIV-1 and HIV-2 are related evolutionarily, nucleic acid sequence analysis reveals that HIV-2 is more closely related to SIV than it is to HIV-1. Guyader et al. (1987) noted only 42% overall genomic sequence identity between the HIV-1 and HIV-2 isolates they compared. Patients infected with HIV-2 can manifest disorders that typify AIDS, purely neurologic disease or asymptomatic infections (Kuhnel et al., 1988) despite HIV-1-related ultrastructural and biological properties such as in vitro cytopathogenicity and CD4 tropism (Clavel et al., 1986).

The HIV-1 and HIV-2 genomes have a typical retroviral configuration comprising LTR's, gag and env regions that encode viral structural proteins, sequences encoding one or more enzyme, including a reverse transcriptase and other ORF's and regulatory elements. The gag region of HIV-1 encodes a precursor peptide known as p55. p55 is processed to produce among other proteins the major core or capsid protein known as p24. In HIV-2, the analogous E precursor is larger, known as p57, and the major core protein is known as p26. Although a high degree of conservation of the gag proteins of HIV-1 and HIV-2 was expected, Guyader et al. (1987) found only 58% identity of amino acids between HIV-1 and HIV-2 gag proteins. Even among distant isolates of HIV-1 there is a greater than 90% identity of gag proteins. That and other data support the hypothesis that although HIV-1 and HIV-2 are somewhat related, they are nevertheless distinct retroviral species.

Because HIV-1 and possibly HIV-2 have such an impact on the human immune system, it is desirable, in fact imperative that sensitive, rapid diagnostic assays for detecting presence of HIV be available for population screening, quality control in blood banks, diagnosis, furtherance of our understanding of those viruses to assure the goal of obtaining a vaccine and cure, and the like. Because of ease and convenience, it is preferable that the assays be immunology-based, such as ELISA's, and for reproducibility, specificity and consistency that the reagents be monoclonal antibodies and defined antigenic peptides. Because p24 antigenemia has been shown to be an early sign of HIV infection (Kessler et al., 1987; Wall et al., 1987) and the observation that clinical progression of AIDS sequelae is associated with reduction in anti-p24 while patients with AIDS can die with high levels of anti-env titers (Coates et al., 1987), it would be advantageous for the assay to be directed to detecting gag products such as p24/p26.

Weiss et al. (1988) identified human serum samples that contained antibodies specific to HIV-2 gp130 in radioimmunoprecipitation assays and in ELISA's. Those antibodies showed low level HIV-1 crossreactivity in a VSV pseudotype neutralization assay and in a neutralization of C8166 syncytia formation assay.

Minassian et al. described a monoclonal antibody identified as R1C7 that was raised against HIV-2. R1C7, an anti-capsid antibody (p26), reacted not only with the three HIV-2 isolates tested, but with the five HIV-1 isolates and seven SIV isolates that were tested. In immunoblots, R1C7 bound to 55KD and 26KD HIV-2 proteins, to 24KD and 55KD HIV-1 proteins and to a 28KD SIV protein.

Niedrig et al. developed a panel of 29 monoclonal antibodies to HIV-1. One antibody was directed to p17 and its precursor p32 whereas the remainder reacted with p24 and some of those also reacted with p55. The p17 antibody was found to be HIV-1 specific. Of the 28 anti-p24 antibodies, 20 reacted in immunoblots with the corresponding capsid protein (p26) of HIV-2 and five of those also recognized the corresponding SIV protein, p28. Niedrig et al. make no mention of antibody titer, the efficacy of the antibodies in a antigen capture assay or which of the antibodies bind to p26, p55 or both. Furthermore, several of antibodies reacted with a 22KD protein of unknown function in HIV-2 preparations.

Many diagnostic kits and assays have been developed for the detection of HIV-1 in samples of sera, blood, blood products or other body tissues. The assays use a variety of techniques such as Western blot, enzyme-linked immunosorbent assay (ELISA) or indirect immunofluorescent assay and employ either antibodies to whole virus or purified viral antigens, see for example, Gallo et al., U.S. Pat. No. 4,520, 113; Sarngadharan, et al., (1984); and Robert-Guroff et al. (1982).

SUMMARY OF THE INVENTION

The instant invention relates to monoclonal antibodies, the cell lines producing those antibodies, the peptides that comprise the epitopes of those antibodies and assays using those antibodies and peptides for the detection of HIV-1 and HIV-2 gene products as well as SIV gene products. In particular, the antibodies react with the p24/p26 capsid protein. The nonapeptide that comprises an HIV-1 /HIV-2 conserved epitope is disclosed and a capture ELISA using a combination of three monoclonal antibodies that can detect simultaneously HIV-1 and HIV-2 is disclosed.

BRIEF DESCRIPTION OF THE FIGURES

FIG. 4. Diagram of some of the recombinant p24 peptides used to map epitopes.

FIG. 5. Diagram of four regions of p24 to which various monoclonal antibodies bind.

FIG. 8. Diagram depicting epitope mapping using sequential overlapping nonapeptides as antigen in ELISA.

FIG. 9. Composition of the regions that comprise the 7-D4 epitope.

FIG. 11. Graph of sensitivity of a capture ELISA using 6-C10 and 5-B4 with and without 7-D4 on the solid phase to detect p26 of HIV-2.

DETAILED DESCRIPTION OF THE INVENTION

The instant invention relates to monoclonal antibodies and their production, immunoassays and oligopeptides. The methods that were used are known in the art and are discussed only briefly throughout the specification. Suitable methods to practice the invention may be found in *Meth Enzymology* 121, (1986) and other available reference materials.

Preparation of Monoclonal Antibodies

Figure 1:
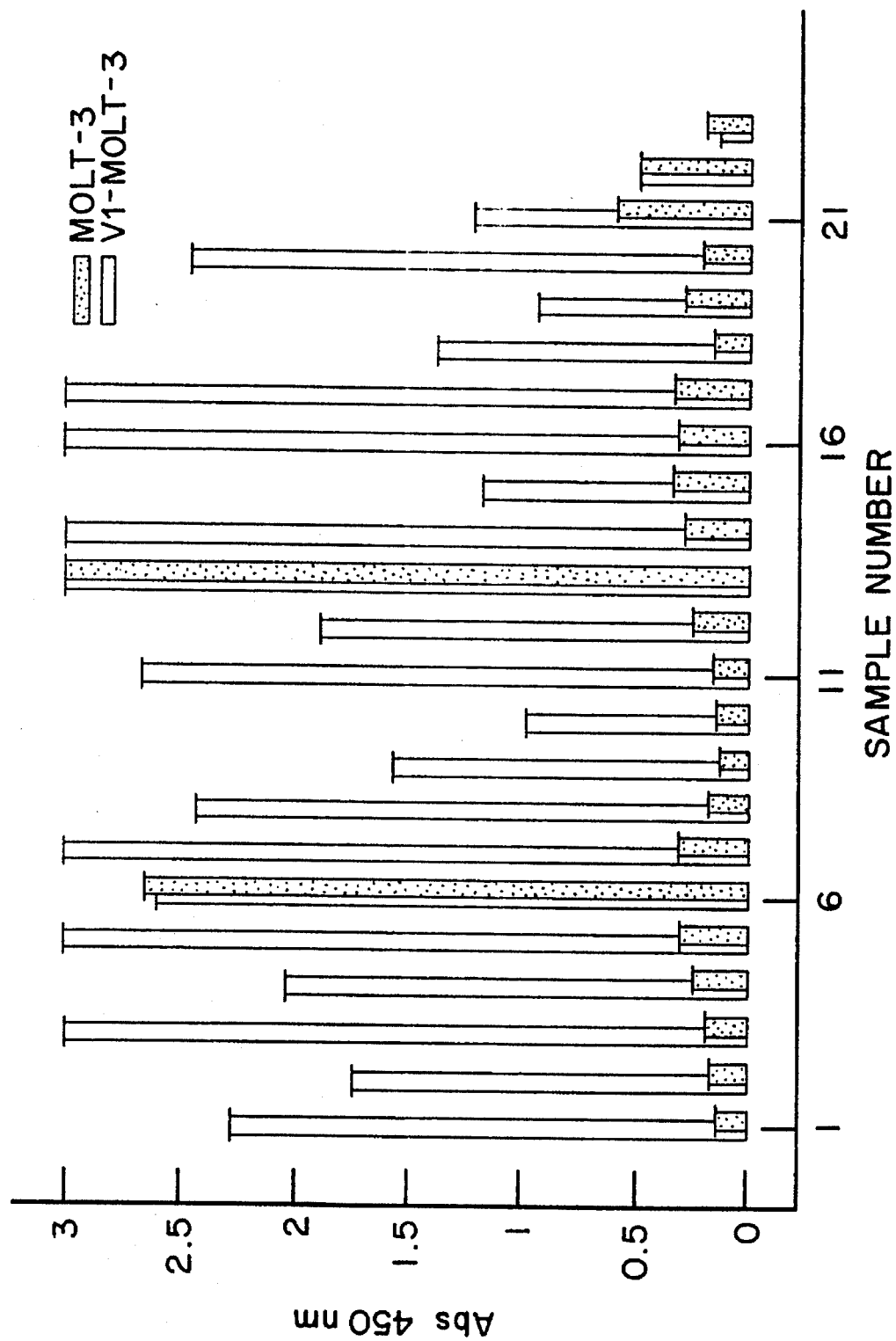
FIG. 1. Graph depicting reactivity of culture supernatants in capture ELISA. A detailed legend appears in Table 1.

Monoclonal antibodies were produced according to established procedures (Kohler & Milstein, 1975). Briefly, female BALB/c mice were immunized intraperitoneally repeatedly with lysates of HIV-1 infected MOLT 3 cells emulsified in complete Freund's adjuvant (50%). Sensitized spleen cells were fused with P3X63-Ag8.653 myeloma cells using PEG 1500. Heterokaryons were selected in HAT medium, cloned and screened for reactivity to HIV antigens in a capture ELISA. The IgG fraction of polyclonal human anti-HIV was coated onto wells of microtiter dishes. HIV-1 (produced in MOLT 3 cells) and culture supernatants were added simultaneously to the wells. Bound murine antibodies were detected with an enzyme-labelled anti-mouse Ig antibody. Data representative of the screening is depicted in FIG. 1. Designation of the sample numbers is set forth in Table 1.

TABLE 1

| ELISA screening of Fusion F86 | |
|---|---|
| Sample No. | Designation |
| 1 | 5-B4 |
| 2 | 5-D9 |
| 3 | 5-E2 |
| 4 | 5-F12 |
| 5 | 6-B9 |
| 6 | 4-E6 |
| 7 | 6-C10 |
| 8 | 6-E11 |
| 9 | 6-F6 |
| 10 | 10-B2 |
| 11 | 10-C12 |
| 12 | 10-D1 |
| 13 | 2-C8 |
| 14 | 7-D4 |

TABLE 1-continued

| ELISA screening of Fusion F86 | |
|---|---|
| Sample No. | Designation |
| 15 | 7-E1 |
| 16 | 7-E10 |
| 17 | 7-F3 |
| 18 | 8-E7 |
| 19 | 9-B7 |
| 20 | 9-D5 |
| 21 | F86 Bleedout* |
| 22 | NMS** |
| 23 | Negative Control |

*Serum obtained at sacrifice
**(Normal Mouse Serum

The hybridoma producing the monoclonal antibody designated 7D4 was deposited at the American Type Culture Collection, Rockville, Md, USA, under the terms of the Budapest Treaty, and was given an identification number of HB 11254.

Western Blots

Figure 2A:
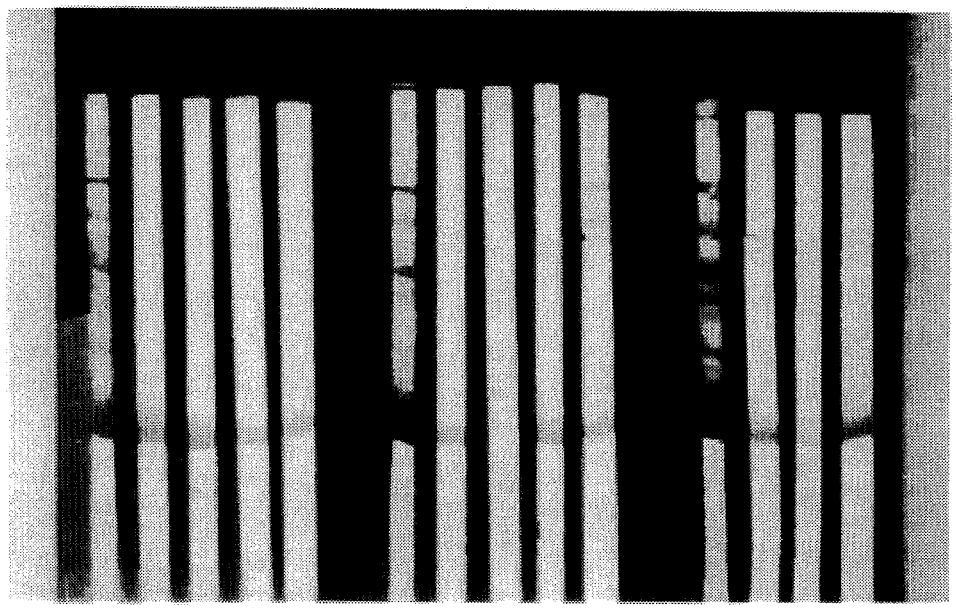
FIGS. 2a and 2b. Photographs of immunoblot nitrocellulose strips determining the specificity of anti-HIV antibodies.
Figure 2B:

Candidate anti-HIV clones were tested further in Western blots (Towbin et al., 1979). Lysates of HIV-infected MOLT 3 cells were separated through a 12% acrylamide gel under denaturing conditions. The proteins were transferred to nitrocellulose and individual strips were blocked and reacted with the culture supernatants. Bound antibody was detected using an enzyme-labelled goat anti-mouse Ig antibody. Antibodies reacting specifically with p24 were selected (FIG. 2). Designation of the strips is set forth in Table 2.

TABLE 2

| Western Blot Analysis of Anti-p24 mAbs | |
|---|---|
| Strip # | Designation |
| 1 | Positive Control |
| 2 | 5-B4 |
| 3 | 5-D9 |
| 4 | 5-E2 |
| 5 | 5-F12 |
| 6 | Positive Control |
| 7 | 6-B9 |
| 8 | 6-C9 |
| 9 | 6-C10 |
| 10 | 6-E11 |
| 11 | Positive Control |
| 12 | 6-F6 |
| 13 | 10-B2 |
| 14 | 10-C12 |
| 15 | Positive Control |
| 16 | 10-D1 |
| 17 | 10-H1 |
| 18 | 7-D4 |
| 19 | Positive Control |
| 20 | 7-E1 |
| 21 | 7-E10 |
| 22 | 7-F3 |
| 23 | 8-E7 |
| 24 | Positive Control |
| 25 | 9-B7 |
| 26 | 9-D5 |

Figure 3:
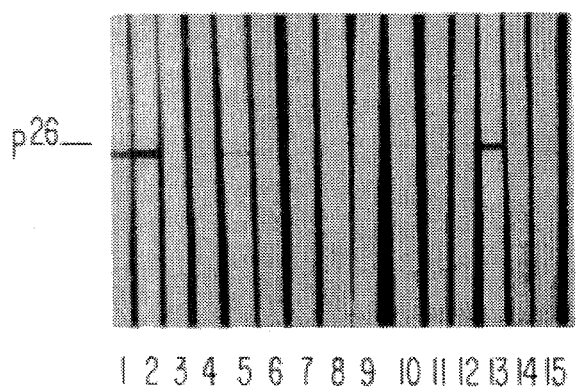
FIG. 3. Protein A-purified antibodies were used as probe to separated HIV-2 proteins in immunoblots. Lanes 1 and 2 are positive controls and Lane 3 is a negative control.

The anti-p24 antibodies were then tested for cross-reactivity to p26 of HIV-2 in immunoblots. HIV-2 lysates were separated, blotted and reacted with the anti-p24 antibodies. Two antibodies, 7-D4 and 5-D9 reacted strongly with p26 (FIG. 3). Designation of the strips is set forth in Table 3.

TABLE 3

Cross-Reactivity of Anti-p24 mAbs with p26 of HIV-2

| Strip | mAb |
|---|---|
| 1 | Hu-anti-HIV-1 IgG |
| 2 | OSS 39-B-3 |
| 3 | MOPC 21 (IgG1) |
| 4 | F86/ 5-B4 |
| 5 | 5-D9 |
| 6 | 6-C10 |
| 7 | 7-E10 |
| 8 | 5-E2 |
| 9 | 9-B7 |
| 10 | 7-F3 |
| 11 | 6-F6 |
| 12 | 9-D5 |
| 13 | 7-D4 |
| 14 | 6-E11 |
| 15 | 7-E1 |

In a related experiment, 7-D4 recognized a protein of approximately 27,000 molecular weight in lysates of SIV-$_{MAC}$.

Epitope Mapping

The amino acids that comprise the p24 epitope of 7-D4 were mapped in the following manner. The gag region and portions of gag were subcloned in an expression vector. Briefly, viral DNA of a $\lambda_{HAT}$ bacteriophage (cDNA library HIV-$1_{RF}$, clone HAT 3 (Starcich et al., (1986)) was digested with EcoRI and by ligation into the pBR322-derived plasmid pMLB1113 to produce a plasmid identified as clone 29 which contained the EcoRI/SstI gag/pol ORF. Clone 29 was digested with SstI to remove extraneous vector sequences and religated to produce plasmid gag/pol 1.2. This latter plasmid was sonicated, blunt-ended and ligated with EcoRI linkers. The mixture was then digested with EcoRI, ligated into λORF8 (Meissner et al. 1987) and packaged. A λORF8 expression library was generated in *E. coli* and screened with a human anti-HIV polyclonal antibody and a mouse anti-p24 (HIV-1) monoclonal antibody. The positives were selected, expanded and the expressed peptides were characterized by Western blotting, immunoassay and nucleotide sequencing. The recombinant p24 peptides gag 8, gag 126, gag 107 and gag 141 were expressed in *E. coli*. Separately, clone 29 was used as a template and oligonucleotides corresponding to the 5' and 3' ends of the published sequence were used in a polymerase chain reaction to generate a complete sequence of the gag protein p24. The 5' end contained an EcoRI site and the 3' end contained a BamHI site. The reaction product was digested with EcoRI and BamHI and then ligated into pMLB1113. A recombinant p24 protein, gag 24.5, was expressed in *E. coli*. The characterization of the recombinant p24 peptides is presented in FIG. 4.

Figure 6A:
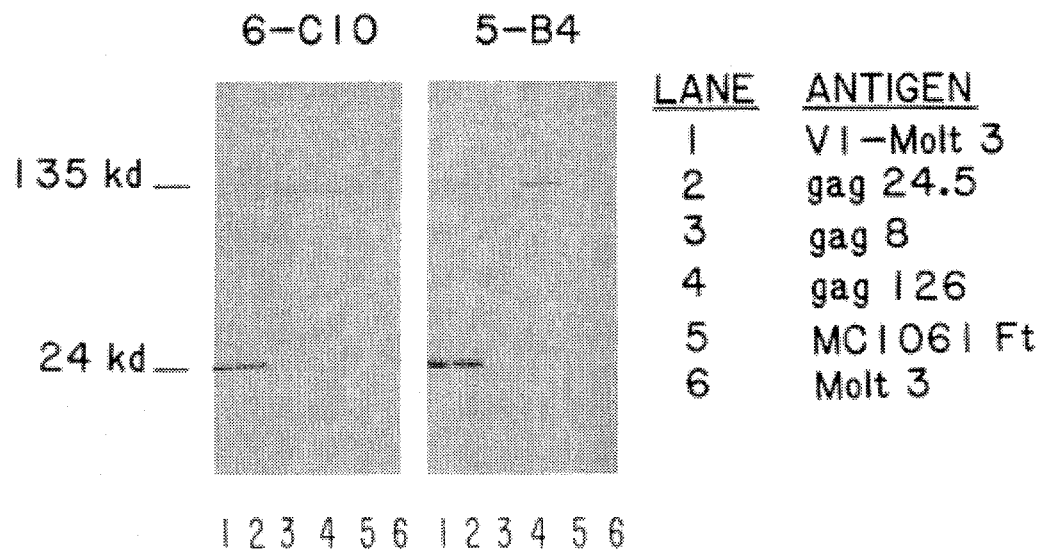
FIGS. 6a and 6b Photographs of Westerns reacting various monoclonals with blotted gag and gag fragments. Lane 1 in each photo contains whole virus lysate. Lane 5 in each photo is a negative control p24⁻ plasmid and Lane 6 in each photo is another negative control containing non-HIV-infected MOLT lysate.
Figure 6B:
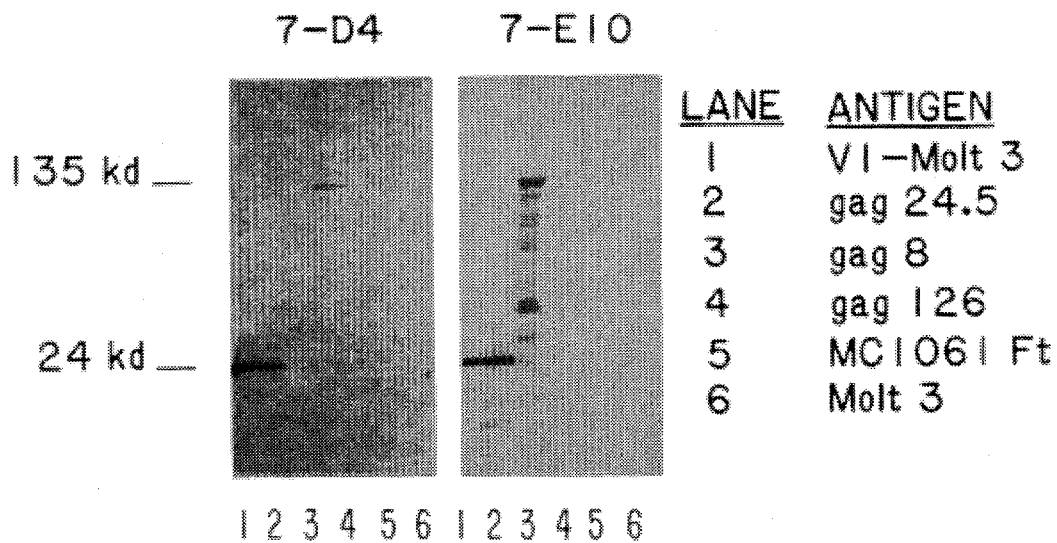

The various recombinant p24 peptides were used as antigen in ELISA's and in Western blots to determine whether or not a given monoclonal antibody bound a given peptide. The reactivity pattern of any one monoclonal antibody with the panel of p24 peptides allowed a localization of the recognized epitope to one of four regions as shown in Table 4 and FIGS. 5 and 6.

TABLE 4

Immunochemical Analysis of Anti-24 mAbs Using Recombinant Peptides

| mAb | gag 24.5 | gag 8 | gag 126 | gag 107 | gag 141 | mAb group |
|---|---|---|---|---|---|---|
| 5-B4 | + | − | + | − | − | B |
| 5-D9 | + | + | + | − | − | C |
| 5-E2 | + | + | − | − | − | D |
| 5-F12 | + | − | + | − | − | B |
| 6-C10 | + | + | + | − | − | C |
| 6-E11 | + | − | − | − | − | A |
| 6-F6 | + | − | − | − | − | A |
| 7-D4 | + | − | + | − | − | B |
| 7-E1 | + | − | + | − | − | B |
| 7-E10 | + | + | − | − | − | D |
| 7-F3 | + | − | + | − | − | B |
| 8-E7 | + | − | − | − | − | A |
| 9-B7 | + | + | − | − | − | D |
| 9-D5 | + | − | − | − | − | A |
| 10-B2 | + | − | + | − | − | B |
| 10-C12 | + | − | − | − | − | A |

Because 7-D4 bound only to gag 24.5 and gag 126, it was possible to deduce that the 7-D4 epitope mapped to region B delimited by amino acid residues 142–209.

Figure 7:
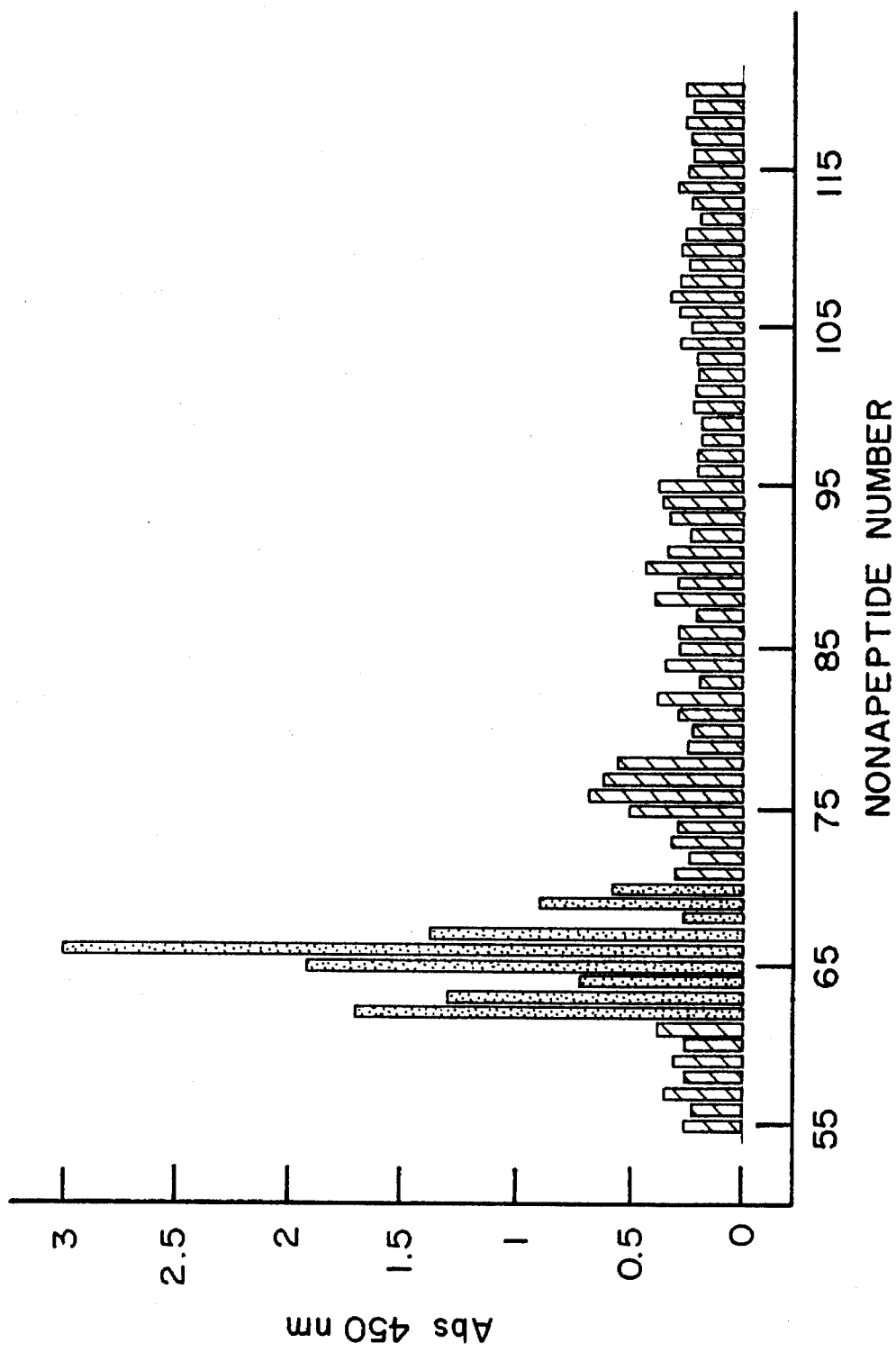
FIG. 7. Graph representing results of ELISA's using sequential overlapping nonapeptides as antigen to determine epitope of 7-D4.

To further localize the epitope of 7-D4, synthetic sequential overlapping nonapeptides were made for the B region of p24. Each nonapeptide served as the solid phase antigen in a series of ELISA's to determine maximal binding affinity of the monoclonal. A single peak of reactivity was found (FIG. 7) for a linear domain comprising the region containing amino acids 142–158 (FIG. 8).

A comparison of the amino acid sequences of p24 of an HIV-1 isolate, p26 of an HIV-2 isolate and p27 of SIV$_{MAC}$ revealed conservation of a decapeptide (FIG. 9) within the epitope of p24 consisting of Ser-Pro-Arg-Thr-Leu-Asn-Ala-Trp-Val-Lys. It can be inferred that the region encompassing the decapeptide is the 7-D4 epitope of p26 in HIV-2 and p27 in SIV$_{MAC}$.

The values of a defined epitope are known to those skilled in the art. One of the benefits is the ability of generating new antibodies capable of reacting with said epitope and similar epitopes. Synthetic peptides are configured after the epitope sequence and either unmodified or conjugated to carriers are used as antigen. For example, peptides can be conjugated to PPD, tetanus toxoid, KLH or BSA using glutaraldehyde, carbodiimide or N-maleimidobenzoyl hydroxuccinimide ester. For a review of using synthetic peptides as antigen, see Ciba Foundation Symposium 119 (1986) John Wiley and Sons, N.Y. Antibodies may be raised in vivo as in mice, goats or other lab animals or in vitro using a system of materials and methods similar to the IVIS of Hana Biologics (Alameda, Calif). Another benefit is that large quantities of the epitope sequence can be produced synthetically or using standard recombinant DNA techniques as described above and the peptides can serve as antigen in immunology-based assays and kits for the detection of circulating antibody or for the detection of circulating antigen in an inhibition type assay. Another benefit relates to improving the assays disclosed herein. Without extending the survey, it is unclear whether the epitope identified in the HIV-1 isolate described herein is specific to that isolate and furthermore to the HIV-2 and SIV isolates described herein. Using that sequence as a reference point, the epitope can be engineered, that is substituting one or more amino acids or alternatively derivitizing the epitope, etc., with a view to identifying a related sequence with a greater degree of conservation among a larger variety of HIV isolates or to obtaining a related sequence with a greater degree of reactivity in assays. Although the nonapeptide analysis apparently identified a discrete linear epitope comprised of amino acids 142–158 of the HIV-1 gag that is conserved in HIV-2 and SIV, it is to be understood that the instant invention relates to monoclonal antibodies, epitopes of said monoclonal antibodies and assays using said antibodies and said peptides that are capable of detecting gag encoded proteins of HIV-1, HIV-2 and SIV.

Capture ELISA Assay

To determine which of the monoclonals would find utility in an ELISA, each was used as a capture or HRP-conjugate antibody in a sandwich assay. Briefly, the monoclonal antibody was coated on wells and 10 µl of disruption buffer added. The antigen samples suspended in detergent buffer or controls in a volume of 100 µl were added next and incubated at 37° C. for 90 minutes. After washing, bound antigen was detected by adding to the wells an enzyme conjugated anti-HIV reagent (horseradish peroxidase-conjugated human anti-HIV IgG, affinity purified, 100 µl) and incubated at 37° C. for 30 minutes. After washing several times, 100 µl of substrate solution were added to the wells and incubated at room temperature for 30 minutes. 100 µl of stop reagent were added and absorbance read at 450 nm using an air blank. Representative data are presented in Table 5.

TABLE 5

Checkerboard Analysis of mAbs

| Capture Antibody | 5B4 | 5D9 | 5E2 | 6C10 | 6E11 | 7E10 | 9B7 | HαHIV |
|---|---|---|---|---|---|---|---|---|
| 5B4 | 0.12 | 0.26 | 0.29 | 0.82 | 0.13 | 1.03 | 0.17 | 2.67 |
| 5D9 | 0.73 | 0.13 | 0.43 | 0.62 | 0.37 | 0.38 | 0.12 | >3.0 |
| 5E2 | 0.58 | 0.47 | 0.14 | 0.61 | 0.23 | 0.80 | 0.11 | 2.51 |
| 6C10 | 0.81 | 0.38 | 0.44 | 0.20 | 0.17 | 0.70 | 0.13 | >3.0 |
| 6E11 | 0.09 | 0.21 | 0.21 | 0.14 | 0.16 | 0.27 | 0.09 | 0.41 |
| 7E10 | 0.84 | 0.43 | 0.49 | 0.84 | 0.18 | 0.18 | 0.13 | >3.0 |
| 9B7 | 0.14 | 0.11 | 0.10 | 0.17 | 0.13 | 0.17 | 0.13 | 0.28 |
| 34A | 0.49 | 0.12 | 0.08 | 0.96 | 0.28 | 1.81 | 0.22 | >3.0 |

Purified mAb were coated overnight at 10 µg/ml. HRP-mAb used at 10 µg/ml added at beginning of incubation (90' at 37° C.).
HRP-human-anti-HIV was added after 60 min.
Absorbances given for 10.0 ng/ml HIV-1 MOLT 3 in NHS.
Absorbance for NHS was 0.12 ± 0.03

Antibodies 5-B4, 6-C10 and 7-E10 worked best as both capture and conjugated antibodies. Maximal signals were obtained with the HRP-human anti-HIV as the conjugate.

Figure 12:
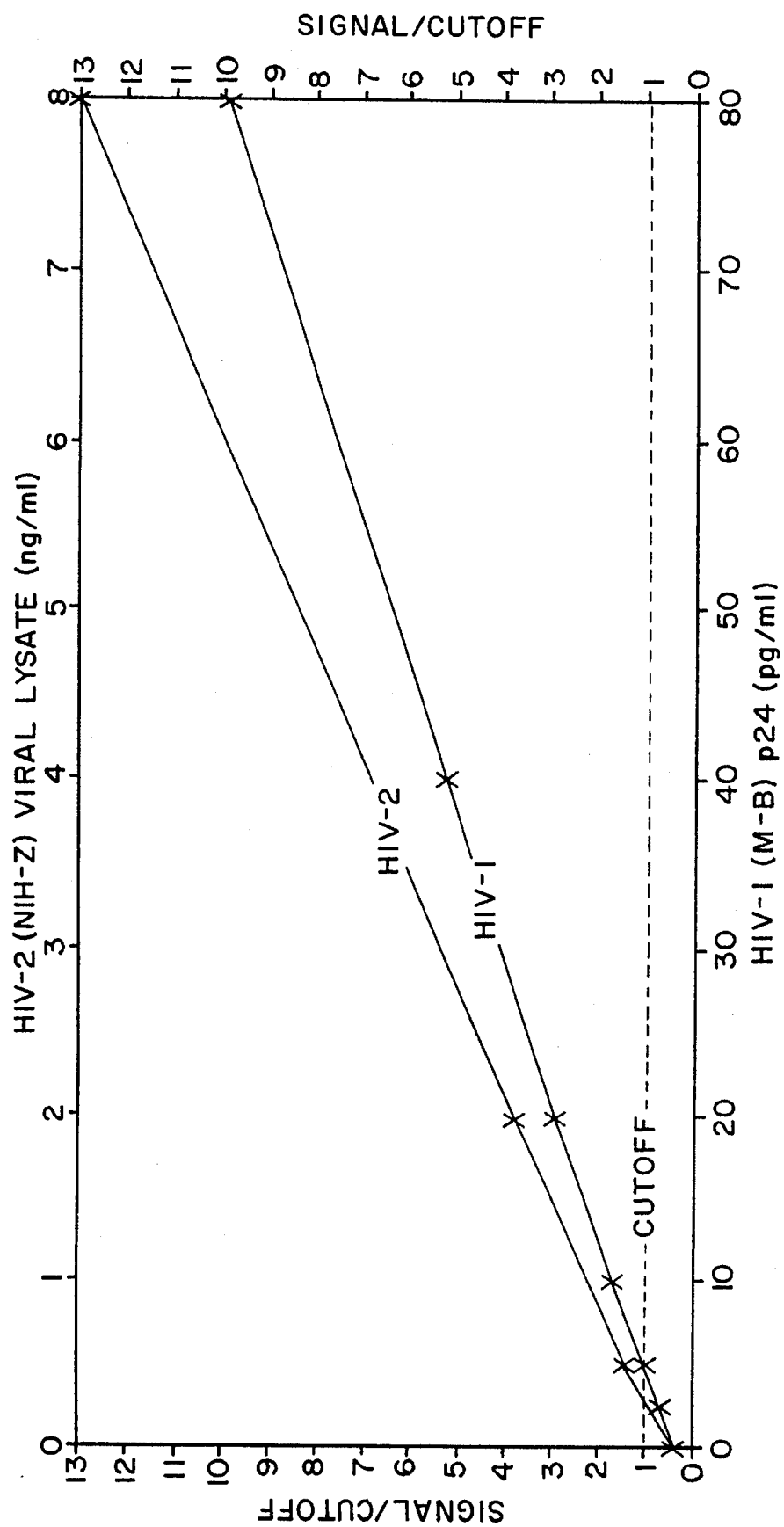
FIG. 12. Dose response curve for HIV-1 and HIV-2 in a capture ELISA using 6-C10, 5-B4 and 7-D4.
Figure 13:
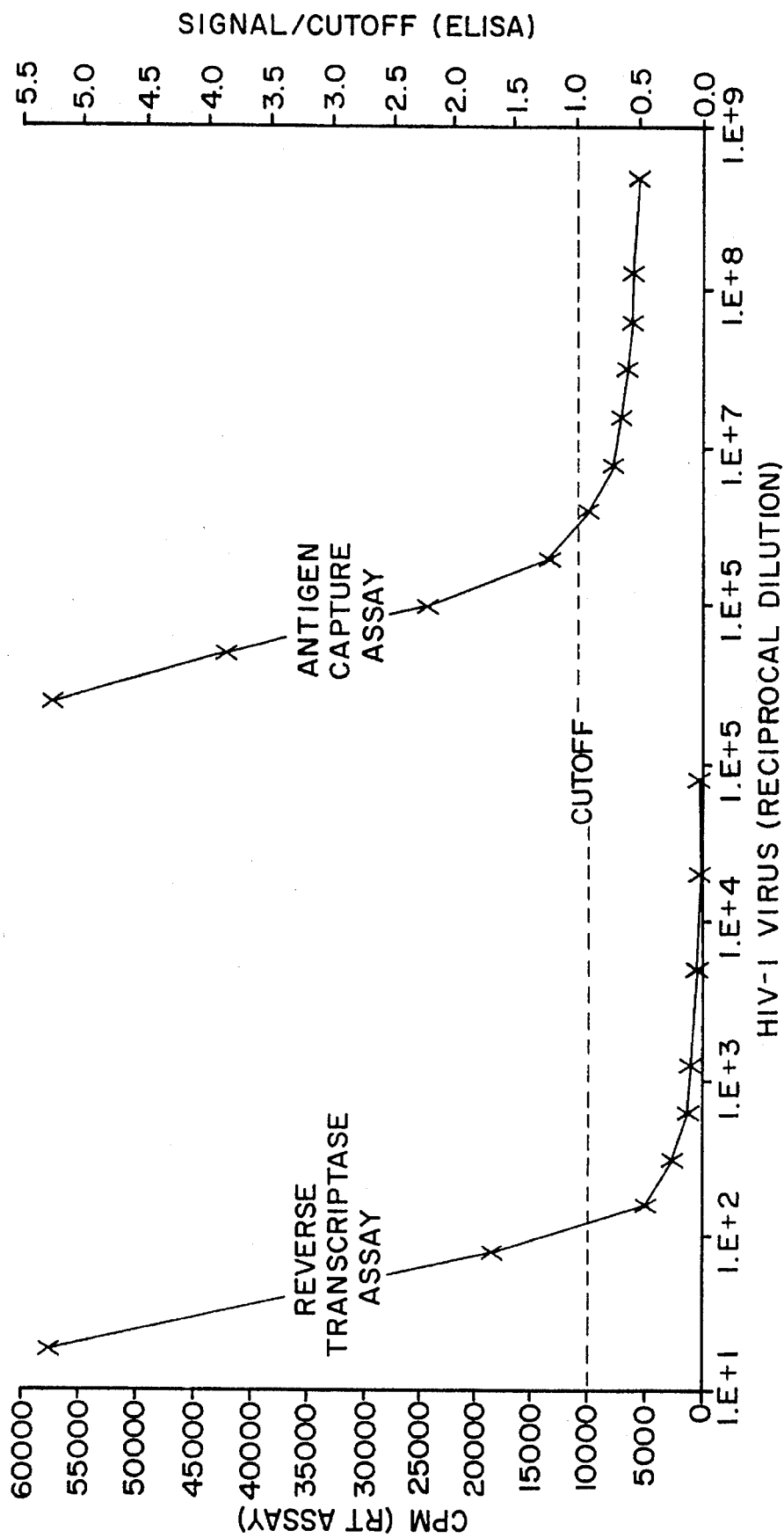
FIG. 13. Comparison of HIV-1 dose response curves between the three antibody capture ELISA and a reverse transcriptase assay.
Figure 10:
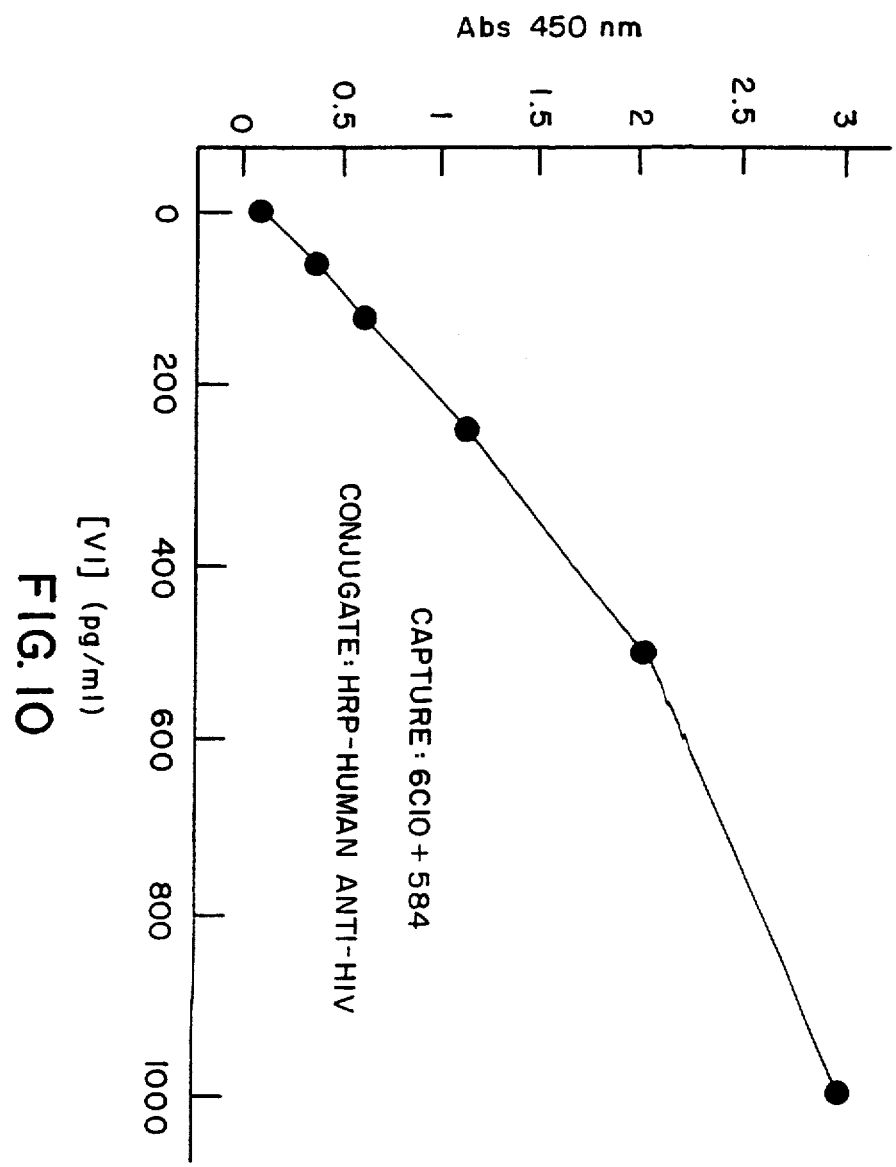
FIG. 10. Graph of sensitivity of a capture ELISA using two anti-p24 antibodies, 6-C10 and 5-B4, on the solid phase and HIV-1 infected MOLT 3 lysate as the antigen. An HRP conjugated human anti-HIV was the reporter.

Various combinations of the monoclonals were used as capture antibodies in ELISA's. The combination of 5-B4 and 6-C10 showed the greatest sensitivity in detecting p24 (FIG. 10). To detect p26 of HIV-2, 7-D4 was used as a capture antibody (FIG. 11). It was found that maximal sensitivity and robustness occurred when the three antibodies, 5-B4, 6-C10 and 7-D4 were combined as capture antibodies. Under those conditions, p26 was detectable as well as p24 from certain borderline clinical samples that were difficult to interpret when only 5-B4 and 6-C10 were used as capture antibodies. The sensitivity of the capture ELISA using these three antibodies is less than 10 pg/ml (less than 1 pg/well) of HIV-1 p24 antigen and less than 0.5 ng/ml of HIV-2 p26 antigen (FIG. 12). The sensitivity is found despite the presence of HIV antibodies in the clinical samples. A capture ELISA using the three antibodies 5-B4, 6-C10 and 7-D4 was also compared to a reverse transcriptase assay for the detection of whole virus. The ELISA was 25,000 times more sensitive than the reverse transcriptase assay (FIG. 13).

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

References

1. Clavel, F., et al., *Science* 233, 343 (1986)
2. Coates, A., et al., *Nature* 326, 549 (1987)
3. Guyader, M., et al., *Nature* 326, 662 (1987)
4. Kessler, H., et al., *J Am Med Assoc* 258, 1196 (1987)
5. Kohler, G, & Milstein, C., at *Nature* 256, 495 (1975)
6. Kuhnel, H., et al., *Proc Natl Acad Sci USA* 86, 2383 (1989)
7. Marlink, R., et al., *AIDS Res Hum Retroviruses* 4, 137 (1988)
8. Minassian, A., et al., *Proc Natl Acad Sci USA* 85, 6939 (1988)
9. Meissner, P. S. et al., *Proc Natl Acad Sci USA* 84, 4171 (1987)
10. Niedrig, M., et al., *J Gen Virol* 69, 2109 (1988)
11. Robert-Guroff, R. C. et al., *Science* 215, 975 (1982)
12. Sarngadharan, M. G., et al., *Science* 224, 506 (1984)
13. Starcich, B. R., et al., *Cell* 45, 637 (1986)
14. Towbin, H. et al., *Proc Natl Acad Sci USA* 76, 4350 (1979)
15. Wall, R., et al., *Lancet i*, 566 (1987)
16. Weiss, R., et al., *AIDS* 2, 95 (1988)

What is claimed is:

1. A monoclonal antibody that cross-reacts with an epitope of p24 of HIV-1 and p26 of HIV-2, said epitope located within amino acid residues 142–158 of p24 based on the numbering depicted in FIG. 9.

2. A diagnostic kit for the detection of HIV-1 and HIV-2, comprising:

(1) a container containing the monoclonal antibody of claim 1; and (2) a container containing a labeled anti-HIV antibody that can detect immunocomplexes of the monoclonal antibody and the antigen of at least one of HIV-1 and HIV-2.

3. The diagnostic kit of claim 1, further comprising an additional monoclonal antibody that reacts with an antigen of HIV-1, wherein said additional monoclonal antibody does not react with said epitope of claim 1.

4. The diagnostic kit of claim 3, wherein said additional monoclonal antibody that reacts with an antigen of HIV-1 binds to an epitope located within amino acid residues 263–344 of p24.

5. A method for detection of HIV-1 and HIV-$_2$ antigens in a sample, comprising contacting said sample with the monoclonal antibody of claim 1, and measuring the formation of antigen-antibody complexes.

6. The method of claim 5, further comprising contacting the sample with an additional monoclonal antibody that has reactivity with an epitope of HIV-1 other than the epitope of the monoclonal antibody of claim 5, prior to measuring the formation of antigen-antibody complexes.

7. The method of claim 6, wherein the additional monoclonal antibody binds with an epitope located within amino acid residues 263–344 of p24, based on the numbering depicted in FIG. 5.

8. A method for detection of HIV-1 and HIV-2 antigens in a sample, which comprises contacting said sample with the monoclonal antibody of claim 1, and an additional antibody that reacts with an antigen of HIV-1 or HIV-2 but does not react with the epitope to which the monoclonal antibody of claim 1 reacts, and measuring the formation of antigen-antibody complexes.

9. A monoclonal antibody according to claim 1, wherein said monoclonal antibody is 7-D4.

10. A cell line for producing the monoclonal antibody according to claim 9, having ATCC Accession Number HB 11254.

11. The diagnostic kit of claim 2, wherein said monoclonal antibody is monoclonal antibody 7-D4.

12. The method of claim 8, comprising contacting the sample with the monoclonal antibody 7-D4.

* * * * *

UNITED STATES PATENT AND TRADEMARK OFFICE
CERTIFICATE OF CORRECTION

PATENT NO. : 5,514,541         Page 1 of 2
DATED      : May 7, 1996
INVENTOR(S) : Butman et al.

It is certified that error appears in the above-indentified patent and that said Letters Patent is hereby corrected as shown below:

Column 8:
    Please correct claim 3, line 1, by deleting "claim 1" and replacing with -- claim 2 --,
                                        line 4, by deleting "claim 1" and replacing with -- claim 2 --; and In the Drawing:
    in "Sheet 9 of 12", by deleting Figure 9 and replacing with -- Figure 10 --.

Signed and Sealed this

Third Day of September, 1996

Attest:

BRUCE LEHMAN

Attesting Officer    Commissioner of Patents and Trademarks